(12) United States Patent
Kinsho et al.

(10) Patent No.: US 6,509,481 B2
(45) Date of Patent: Jan. 21, 2003

(54) TETRAHYDROFURAN COMPOUNDS HAVING ALICYCLIC STRUCTURE

(75) Inventors: Takeshi Kinsho, Nakakubiki-gun (JP); Koji Hasegawa, Nakakubiki-gun (JP); Takeru Watanabe, Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/117,218

(22) Filed: Apr. 8, 2002

(65) Prior Publication Data

US 2002/0183529 A1 Dec. 5, 2002

(30) Foreign Application Priority Data

Apr. 9, 2001 (JP) ........................................ 2001-109755

(51) Int. Cl.$^7$ ........................ C07D 315/00; C07D 307/00
(52) U.S. Cl. ........................................ 549/331; 549/429
(58) Field of Search .................... 549/331, 429

(56) References Cited

PUBLICATIONS

Suzuki, Hideo, 'Preparation of tetracycolo[6.2.1.13,6.02,7]dodecane–4,5–dicarboxylic acid diester' CA 135:19396 (2001).*
Takeuchi, Hitomi et al, 'Preparation of N–(acryloyloxy)hexahydrophthalimides for UV–curable polymer compositions' CA 133:207807 (2000).*
Noire, Paul D., 'Preparation of cycloalkyltetrahydrofurans and analogs as perfume fragrance' CA 125:86473 (1996).*

* cited by examiner

Primary Examiner—Amelia Owens
(74) Attorney, Agent, or Firm—Millen, White, Zelano & Branigan, P.C.

(57) ABSTRACT

Tetrahydrofuran compounds of formula (1) wherein the broken line represents a single bond, a divalent organic group, or a structure in which the alicyclic structure in the form of norbornene or tetracyclo[4.4.0.1$^{2,5}$.1$^{7,10}$]dodecene and the tetrahydrofuran cyclic structure share one or two constituent carbon atoms, and k is 0 or 1 are novel and useful as monomers to form base resins for use in chemically amplified resist compositions adapted for micropatterning lithography

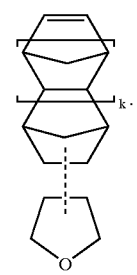

(1)

4 Claims, No Drawings

TETRAHYDROFURAN COMPOUNDS HAVING ALICYCLIC STRUCTURE

This invention relates to novel tetrahydrofuran compounds useful as monomers to form base resins for use in chemically amplified resist compositions adapted for micropatterning lithography.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 $\mu$m or less.

The resist materials for use in photolithography using light of an excimer laser, especially ArF excimer laser having a wavelength of 193 nm, are, of course, required to have a high transmittance to light of that wavelength. In addition, they are required to have an etching resistance sufficient to allow for film thickness reduction, a high sensitivity sufficient to eliminate any extra burden on the expensive optical material, and especially, a high resolution sufficient to form a precise micropattern. To meet these requirements, it is crucial to develop a base resin having a high transparency, rigidity and reactivity. None of the currently available polymers satisfy all of these requirements. Practically acceptable resist materials are not yet available.

Known high transparency resins include copolymers of acrylic or methacrylic acid derivatives and polymers containing in the backbone an alicyclic compound derived from a norbornene derivative. All these resins are unsatisfactory. For example, copolymers of acrylic or methacrylic acid derivatives are relatively easy to increase reactivity in that highly reactive monomers can be introduced and acid labile units can be increased as desired, but difficult to increase rigidity because of their backbone structure. On the other hand, the polymers containing an alicyclic compound in the backbone have rigidity within the acceptable range, but are less reactive with acid than poly(meth)acrylate because of their backbone structure, and difficult to increase reactivity because of the low freedom of polymerization. Additionally, since the backbone is highly hydrophobic, these polymers are less adherent when applied to substrates. Therefore, some resist compositions which are formulated using these polymers as the base resin fail to withstand etching although they have satisfactory sensitivity and resolution. Some other resist compositions are highly resistant to etching, but have low sensitivity and low resolution below the practically acceptable level.

SUMMARY OF THE INVENTION

An object of the invention is to provide a novel tetrahydrofuran compound useful as a monomer to form a polymer for use in the formulation of a photoresist composition which exhibits firm adhesion and high transparency when processed by photolithography using light with a wavelength of less than 300 nm, especially ArF excimer laser light as the light source.

We have found that a tetrahydrofuran compound of formula (1), (2), (3) or (4) can be prepared in high yields by a simple method to be described later, that a polymer obtained from this tetrahydrofuran compound has high transparency at the exposure wavelength of an excimer laser, and that a resist composition comprising the polymer as a base resin is improved in adhesion to substrates.

The present invention provides a tetrahydrofuran compound of the following general formula (1).

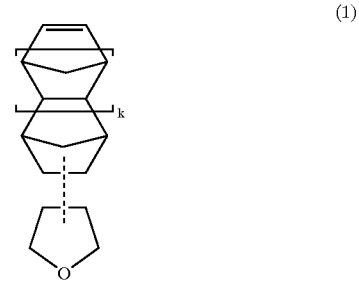

(1)

Herein the broken line represents a single bond, a divalent organic group, or a structure in which the alicyclic structure in the form of norbornene or tetracyclo[4.4.0.1$^{2,5}$.1$^{7,10}$] dodecene and the tetrahydrofuran cyclic structure share one or two constituent carbon atoms, and k is 0 or 1.

In one embodiment, the invention provides a tetrahydrofuran compound having the following general formula (2).

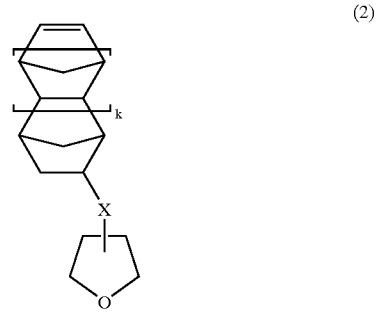

(2)

Herein X is a single bond or a group —(CH$_2$)$_m$— in which one or more methylene groups may be replaced by one or more oxygen atoms, m is an integer of 1 to 8, and k is 0 or 1.

Another embodiment is a tetrahydrofuran compound having the following general formula (3).

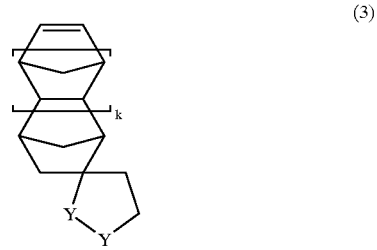

(3)

Herein one of two Y's is an oxygen atom and the other is a methylene group, and k is 0 or 1.

A further embodiment is a tetrahydrofuran compound having the following general formula (4):

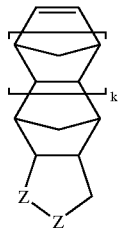
(4)

Herein one of two Z's is an oxygen atom and the other is a methylene group, and k is 0 or 1.

DESCRIPTION OF THE PREFERRED EMBODIMENT

The tetrahydrofuran compounds of the present invention have the general formula (1).

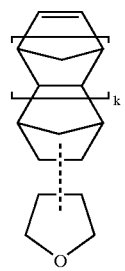
(1)

Herein, the broken line represents a single bond, a divalent organic group, or a structure in which the alicyclic structure in the form of norbornene or tetracyclo[$4.4.0.1^{2,5}.1^{7,10}$] dodecene and the tetrahydrofuran cyclic structure share one or two constituent carbon atoms, and k is 0 or 1.

The divalent organic group is preferably a group —$(CH_2)_m$— in which one or more methylene groups may be replaced by one or more oxygen atoms, wherein m is an integer of 1 to 8. Therefore, the preferred tetrahydrofuran compounds are those of the general formula (2).

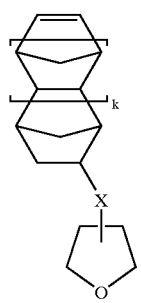
(2)

Herein X is a single bond or a group —$(CH_2)_m$— in which one or more methylene groups may be replaced by one or more oxygen atoms, m is an integer of 1 to 8, and k is 0 or 1.

Those tetrahydrofuran compounds of the general formulae (3) and (4) are also preferred.

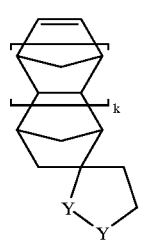
(3)

Herein one of two Y's is an oxygen atom and the other is a methylene group, and k is 0 or 1.

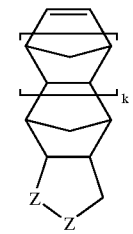
(4)

Herein one of two Z's is an oxygen atom and the other is a methylene group, and k is 0 or 1.

Illustrative examples of the inventive tetrahydrofuran compound are given below.

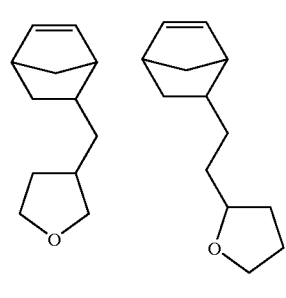

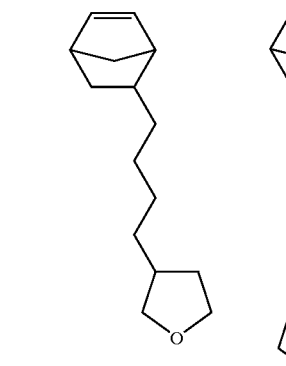

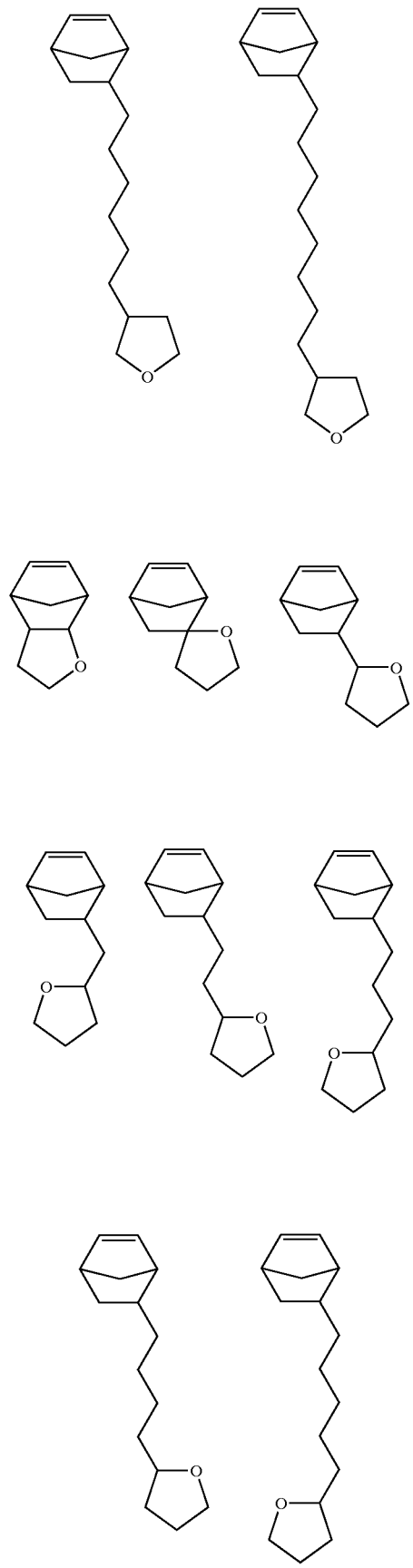
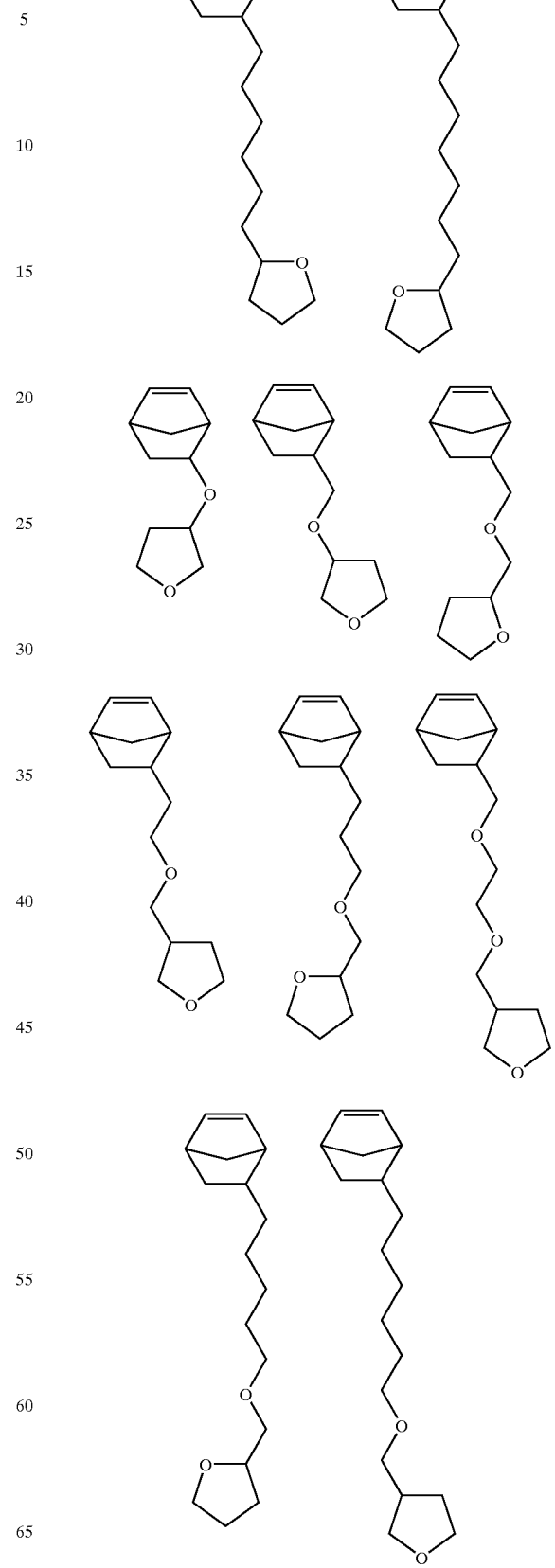

-continued

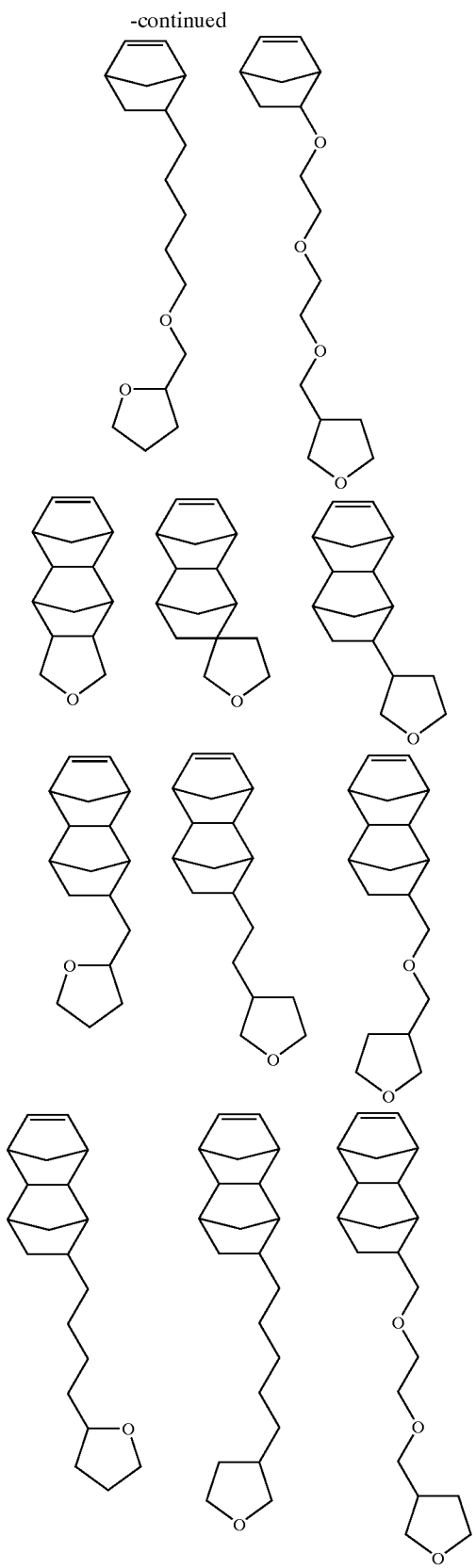

It is believed that resist polymers obtained using these tetrahydrofuran compounds as the monomer exhibit good adhesion to substrates because the tetrahydrofuran moiety regarded as a polar group that brings out adhesion is positioned at a site separated apart from the polymer backbone by a linker such as an alkylene group. By selecting a tetrahydrofuran compound having a linker of optimum length and type as the monomer to form a polymer, the polymer as a whole can be adjusted to an appropriate lipophilicity and controlled in dissolution properties.

The tetrahydrofuran compounds of the invention can be produced by the following three methods, for example, but the invention is not limited to these methods.

The first method is synthesis by intramolecular dehydration/cyclization reaction of a corresponding diol compound (5).

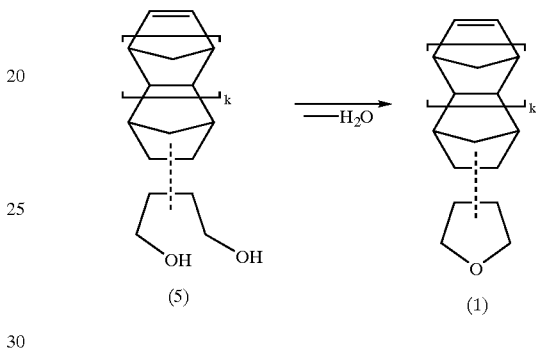

Herein the broken line and k are as defined above.

Better results are obtained from intramolecular dehydration reaction when an acid or a salt thereof, or a phosphorus reagent is used.

Examples of the acid used herein include inorganic acids such as hydrochloric acid, hydrobromic acid, sulfuric acid, nitric acid, perchloric acid, and phosphoric acid and organic acids such as formic acid, acetic acid, benzoic acid, p-toluenesulfonic acid, and benzenesulfonic acid, and salts thereof as well as cation-exchange resins. Examples of the phosphorus reagent include hexamethylphosphoric triamide (HMPA), dialkyl azodicarboxylate-triphenylphosphine, triethylphosphine, and potassium carbonate-triphenylphosphine.

The second method involves the steps of converting a diol compound (5) to a compound (6) having a leaving group such as a halogen atom, alkylsulfonyloxy group or arylsulfonyloxy group, and treating the compound (6) with a base for cyclization into a tetrahydrofuran compound (1).

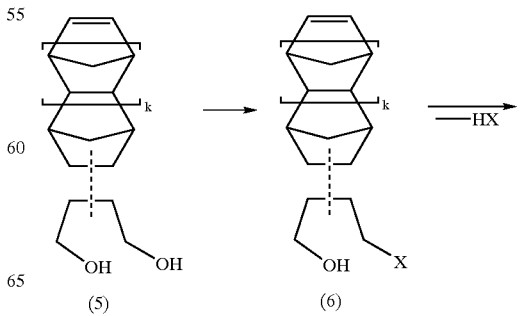

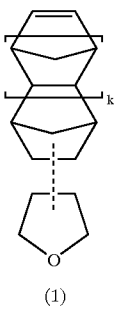

(1)

Herein, X is a halogen atom, alkylsulfonyloxy group or arylsulfonyloxy group, and the broken line and k are as defined above.

The first step is to synthesize the compound (6) having a leaving group. Since the compound (5) has two primary hydroxyl groups in the molecule, only one of which should be converted to a leaving group X, the amounts of reagents and reaction conditions must be carefully determined.

In the case of the compound (6) having a leaving group X which is a halogen atom, X is preferably chlorine or bromine. In this case, various well-known methods are applicable to the synthesis of haloalcohol compound (6) from diol compound (5). Some exemplary methods use hydrohalogenic acids such as hydrochloric acid and hydrobromic acid, sulfur reagents such as thionyl chloride and thionyl bromide, and phosphorus reagents such as phosphorus trichloride, phosphorus pentachloride, phosphorus tribromide or triphenylphosphine combined with various halogen sources.

In the case of the compound (6) having a leaving group X which is an alkylsulfonyloxy or arylsulfonyloxy group, X is preferably a methanesulfonyloxy, trifluoromethanesulfonyloxy, benzenesulfonyloxy or p-toluenesulfonyloxy group for availability of their starting materials. In this case, the sulfonyloxy compound (6) is conventionally synthesized by reacting a corresponding sulfonyl halide with the diol compound (5) in a solvent in the presence of a base.

It is also possible to convert the compound (6) wherein X is an alkylsulfonyloxy or arylsulfonyloxy group to the haloalcohol compound (6) wherein X is halogen. In this case, reaction with a halide salt such as lithium chloride, lithium bromide, sodium bromide or calcium bromide may be carried out in a polar solvent such as dimethylformamide (DMF), dimethyl sulfoxide (DMSO) or ethanol at room temperature or elevated temperature.

The second step is for a base to act on the compound (6) having a leaving group X in a solvent to produce the desired tetrahydrofuran compound. Examples of the base used herein include alkoxides such as sodium methoxide, sodium ethoxide, lithium methoxide, lithium ethoxide, lithium tert-butoxide and potassium tert-butoxide; organic amines such as pyridine, triethylamine, N,N-dimethylaniline and 4-dimethylaminopyridine; inorganic hydroxides such as sodium hydroxide, lithium hydroxide, potassium hydroxide, barium hydroxide and tetra-n-butylammonium hydroxide; inorganic carbonates such as sodium carbonate, sodium hydrogen carbonate, lithium carbonate and potassium carbonate; alkyl metal compounds such as trityllithium, tritylsodium, tritylpotassium, methyllithium, phenyllithium, n-butyllithium, sec-butyllithium, tert-butyllithium and ethyl magnesium bromide; and metal amides such as sodium amide, potassium amide, lithium diisopropylamide, potassium diisopropylamide, lithium dicyclohexylamide, potassium dicyclohexylamide, lithium 2,2,6,6-tetramethylpiperidine, lithium bistrimethylsilylamide, sodium bistrimethylsilylamide, potassium bistrimethylsilylamide, lithium isopropylcyclohexylamide and bromomagnesium diisopropylamide.

In the event where compound (6) is synthesized in the first step using a base, it can be further converted to compound (1) without isolation of the intermediate (6).

The third method is the synthesis of the desired tetrahydrofuran compound (2) from a tetrahydrofuran compound (7) and an alicyclic compound (8).

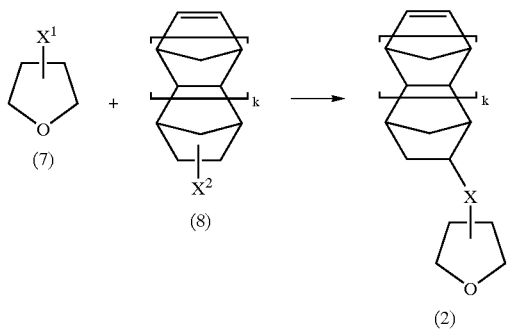

Herein, $X^1$ and $X^2$ are groups which react with each other to form X, and X and k are as defined above.

$X^1$ and $X^2$ differ depending on the structure of X in the target compound. In one example wherein $X^1$ and $X^2$ are a haloalkyl group and an organometallic alkyl group, the compound (2) is synthesized through coupling reaction of these groups. In another example wherein $X^1$ and $X^2$ are a haloalkyl group and a hydroxyalkyl group, the compound (2) is synthesized through ether formation or O-alkylation reaction. One exemplary reaction scheme is shown below.

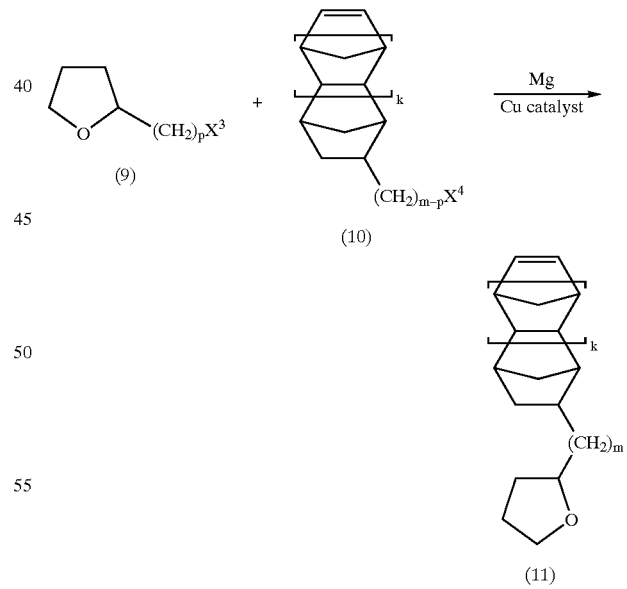

Herein, $X^3$ and $X^4$ are halogen atoms, p is an integer of $1 \leq p \leq m$, and k and m are as defined above. In this process, either one of halide compounds (9) and (10) forms a Grignard reagent with magnesium, which undergoes coupling reaction with the other halide compound in the presence of a copper catalyst, yielding the tetrahydrofuran compound (11).

Another exemplary reaction scheme is shown below.

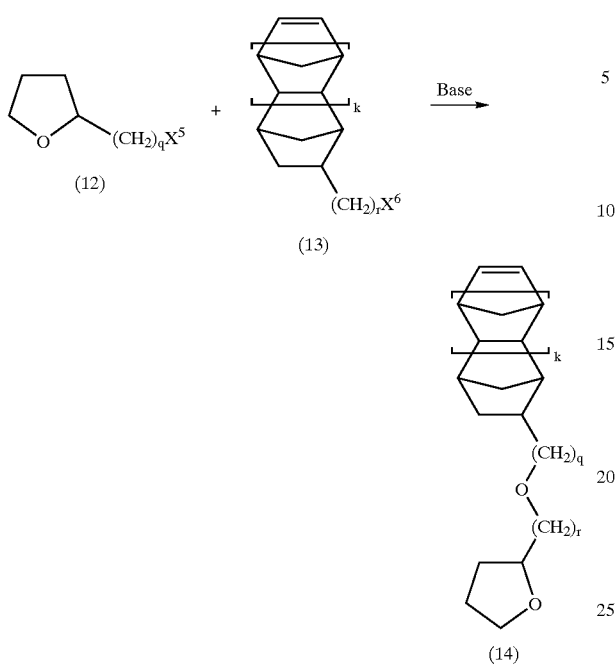

Herein, one of $X^5$ and $X^6$ is a hydroxyl group and the other is a halogen atom, q and r are integers satisfying $1 \leq q+r+1 \leq m$, and k and m are as defined above. In this process, compounds (12) and (13) are treated with a base to effect carbon-oxygen bond-forming reaction or etherification, yielding the desired tetrahydrofuran compound (14).

A polymer or high molecular weight compound is prepared using the inventive tetrahydrofuran compound as a monomer. The method is generally by mixing the monomer with a solvent, adding a catalyst or polymerization initiator, and effecting polymerization reaction while heating or cooling the system if necessary. This polymerization reaction can be effected in a conventional way. Exemplary polymerization processes are ring-opening metathesis polymerization, addition polymerization, and alternating copolymerization with maleic anhydride or maleimide. It is also possible to copolymerize the tetrahydrofuran compound with another norbornene monomer.

A resist composition is formulated using as a base resin the polymer resulting from polymerization of the tetrahydrofuran compound. Usually, the resist composition is formulated by adding an organic solvent and a photoacid generator to the polymer and if necessary, further adding a crosslinker, a basic compound, a dissolution inhibitor and other additives. Preparation of the resist composition can be effected in a conventional way.

The resist composition formulated using the polymer resulting from polymerization of the inventive tetrahydrofuran compound lends itself to micropatterning with electron beams or deep-UV rays since it is sensitive to high-energy radiation and has excellent sensitivity, resolution, and etching resistance. Especially because of the minimized absorption at the exposure wavelength of an ArF or KrF excimer laser and firm adhesion to the substrate, a finely defined pattern having sidewalls perpendicular to the substrate can easily be formed. The resist composition is thus suitable as micropatterning material for VLSI fabrication.

EXAMPLE

Synthesis Examples and Reference Examples are given below for further illustrating the invention. It is not construed that the invention be limited to these examples.

Synthesis Examples are first described. Synthesized were tetrahydrofuran compounds within the scope of the invention, designated below as Monomers 1 to 5.

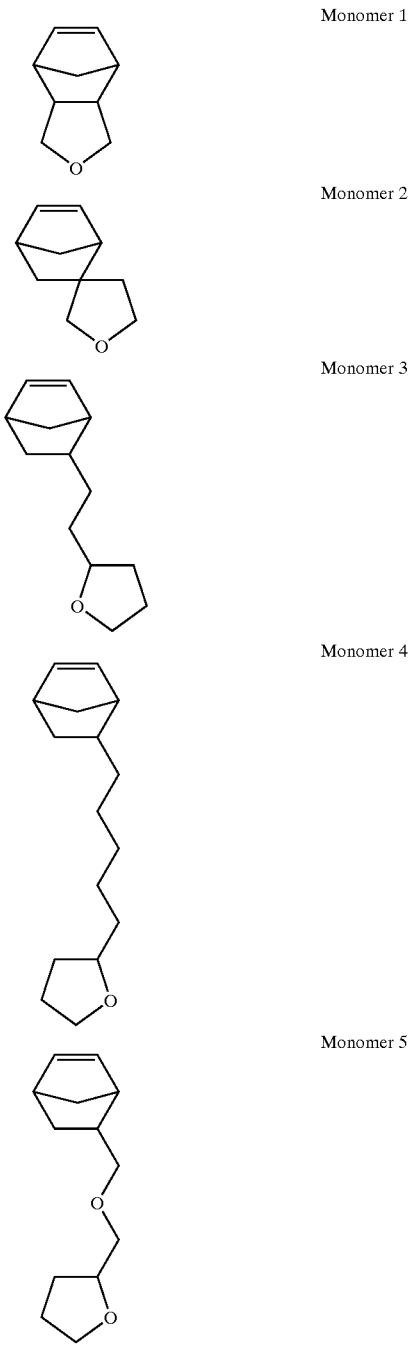

Synthesis Example 1

Synthesis 1 of endo-4-oxatricyclo[$5.2.1.0^{2,6}$]deca-8-ene (Monomer 1)

In 1000 ml of pyridine was dissolved 156 g of cis-5-norbornene-endo-2,3-dimethanol. In a nitrogen atmosphere, the solution was cooled at 5° C., and 200 g of p-toluenesulfonyl chloride was added thereto. The solution was stirred at the temperature for one hour and then at room temperature for 8 hours. The reaction mixture was poured into dilute hydrochloric acid, followed by extraction with ethyl acetate. The ethyl acetate solution was washed with a saturated sodium chloride solution, dried over magnesium sulfate, and concentrated in vacuum, yielding crude 2-hydroxymethyl-3-p-toluenesulfonyloxymethyl-5-norbornene. The crude product was dissolved in 800 ml of toluene, which was added dropwise to a mixture of 450 g of an aqueous 26% sodium hydroxide solution and 1 g of tetra-n-butylammonium chloride. The resulting mixture was stirred at room temperature for 12 hours. Thereafter, the toluene layer was separated, washed with water and saturated sodium chloride solution, dried over magnesium sulfate, concentrated in vacuum, and purified by silica gel column chromatography, obtaining 98 g (yield 71%) of the desired compound (endo-isomer).

IR (liquid film): v=3061, 2962, 2863, 1097 $cm^{-1}$ $^1$H-NMR (300 MHz in $CDCl_3$): δ=1.42 (1H, d, J=8.3 Hz), 1.50 (1H, d, J=8.3 Hz), 2.80–2.92 (4H, m), 3.37–3.46 (2H, m), 3.50–3.60 (2H, m), 6.15–6.25 (2H, m) ppm Synthesis Example 2

Synthesis 2 of endo-4-oxatricyclo[5.2.1.0$^{2,6}$]deca-8-ene (Monomer 1)

In 3000 ml of carbon tetrachloride were dissolved 312 g of cis-5-norbornene-endo-2,3-dimethanol and 576 g of triphenylphosphine. With stirring, the solution was heated to reflux for 28 hours. After cooling, 2000 ml of n-hexane was added to the reaction mixture whereupon the triphenylphosphine oxide formed was filtered off. The filtrate was concentrated in vacuum and purified by silica gel column chromatography, obtaining 243 g (yield 88%) of the desired compound (endo-isomer). This compound had physical properties and spectra which were identical with those of Synthesis Example 1.

Synthesis Example 3

Synthesis of spiro[5-norbornene-2,3'-tetrahydrofuran]

(Monomer 2)

Reaction was carried out under the same conditions as in Synthesis Example 1 except that 2-hydroxyethyl-2-hydroxymethyl-5-norbornene (a mixture of 9:1 isomers) was used instead of cis-5-norbornene-endo-2,3-dimethanol in Synthesis Example 1. The crude product was distilled in vacuum, obtaining the desired compound (a mixture of 9:1 isomers) in a yield of 68%.

Boiling point: 65° C./665 Pa

IR (liquid film): v=3057, 2964, 2935, 2864, 1074 $cm^{-1}$ $^{13}$C-NMR (300 MHz, $CDCl_3$) of major isomer, (1R*,2S*,4R*)-spiro[5-norbornene-2,3'-tetrahydrofuran]: δ=37.95, 40.84, 42.32, 48.96, 49.45, 49.99, 67.99, 79.64, 134.69, 138.06 ppm $^{13}$C-NMR (75.58 MHz, $CDCl_3$) of minor isomer, (1R*,2R*,4R*)-spiro[5-norbornene-2,3'-tetrahydrofuran]: δ=40.66, 41.70, 42.80, 48.99, 49.67, 49.86, 68.01, 77.38, 134.46, 138.11 ppm Synthesis Example 4

Synthesis of 2-[2-(tetrahydrofuran-2-yl)ethyl]-5-norbornene (Monomer 3)

In a nitrogen atmosphere, 400 g of tetrahydrofurfuryl bromide, 250 mg of copper (I) iodide and 650 mg of triethyl phosphate were dissolved in 1500 ml of tetrahydrofuran, which was stirred at 5° C. A Grignard reagent, which had been prepared from 575 g of 2-bromomethyl-5-norbornene (a mixture of 9:1 endo/exo-forms), 75 g of magnesium and 1500 ml of tetrahydrofuran, was added dropwise to the solution while the solution was kept below 20° C. The mixture was stirred at 5° C. for 2 hours, then at 50° C for 5 hours, after which the reaction mixture was poured into an aqueous saturated ammonium chloride solution, followed by extraction with ethyl acetate. The ethyl acetate solution was washed with an aqueous saturated sodium hydrogen carbonate solution and a saturated sodium chloride solution, dried over magnesium sulfate, and concentrated in vacuum. This was followed by vacuum distillation for purification, obtaining 407 g (yield 69%) of the desired compound (a mixture of 9:1 endo/exo-forms).

Boiling point: 92° C./93 Pa

IR (liquid film): v=3057, 2964, 2935, 2864, 1240, 1074 $cm^{-1}$

EI-mass spectrum (70 eV): $(m/z)^+$=43, 66, 91, 109, 127, 192 ($M^+$)

Synthesis Example 5

Synthesis of 2-[5-(tetrahydrofuran-2-yl)pentyl]-5-norbornene (Monomer 4)

Reaction was carried out under the same conditions as in Synthesis Example 4 except that 2-(4-chlorobutyl)-5-norbornene (a mixture of 9:1 endo/exo-forms) was used instead of 2-bromomethyl-5-norbornene. The product was purified by silica gel column chromatography, obtaining the desired compound (a mixture of 9:1 endo/exo-forms) in a yield of 59%.

EI-mass spectrum (70 eV): $(m/z)^+$=43, 66, 95, 109, 151, 1169, 234 ($M^+$)

Synthesis Example 6

Synthesis of 2-(tetrahydrofurfuryloxymethyl)-5-norbornene (Monomer 5)

In a nitrogen atmosphere, 20.8 g of 5-norbornene-2-methanol (a mixture of 9:1 endo/exo-forms) was added to 170 ml of 1.0M dimsyl sodium/dimethylsulfoxide solution at 80° C. After evolution of hydrogen ceased, 500 mg of potassium iodide was added to the solution, and 27 g of tetrahydrofurfuryl bromide was added dropwise. The reaction mixture was stirred at 80° C. for 12 hours, and poured into dilute hydrochloric acid, followed by extraction with ethyl acetate. The ethyl acetate solution was washed with an aqueous saturated sodium hydrogen carbonate solution and a saturated sodium chloride solution, dried over magnesium sulfate, and concentrated in vacuum. It was further purified by silica gel column chromatography, obtaining 21 g (yield 62%) of the desired compound (a mixture of 9:1 endo/exo-forms).

EI-mass spectrum (70 eV): $(m/z)^+$=43, 66, 71, 85, 106, 143, 208 ($M^+$)

CI-mass spectrum (isobutane): $(m/z)^+$=107, 125, 143, 209 $[(M+H)^+]$

Reference Example

Polymers were synthesized using the tetrahydrofuran compounds according to the invention. Resist compositions having the polymers blended as a base resin were examined for substrate adhesion.

Reference Example 1

Synthesis of Polymers

Polymers were synthesized using the tetrahydrofuran compounds obtained in the above Synthesis Examples.

Reference Example 1-1

Synthesis of Polymer 1

A mixture of 13.6 g of Monomer 1, 104.2 g of 2-ethyl-2-norbornyl 5-norbornene-2-carboxylate, 78.4 g of maleic anhydride, and 200 g of tetrahydrofuran was heated at 60° C., to which 7.4 g of 2,2'-azobisisobutyronitrile was added. The mixture was stirred for 15 hours while keeping at 60° C. The reaction mixture was cooled to room temperature, and dissolved in 500 ml of acetone. With vigorous stirring, the reaction mixture was added dropwise to 10,000 ml of isopropyl alcohol. The solids formed were collected by filtration, and dried in vacuum at 40° C. for 15 hours, yielding the end polymer in white solid powder form, designated Polymer 1 below. The amount was 58.0 g and the yield was 35%.

It is noted that Mw is a weight average molecular weight determined by GPC using a polystyrene standard.

Reference Examples 1-2,3

Synthesis of Polymers 2, 3

Polymers 2 and 3 were synthesized according to the same formulation as above using Monomers 2 and 3

Polymer 1

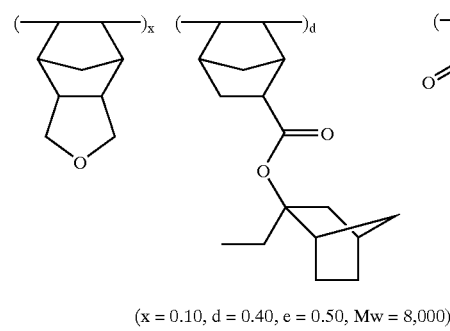

(x = 0.10, d = 0.40, e = 0.50, Mw = 8,000)

Polymer 2

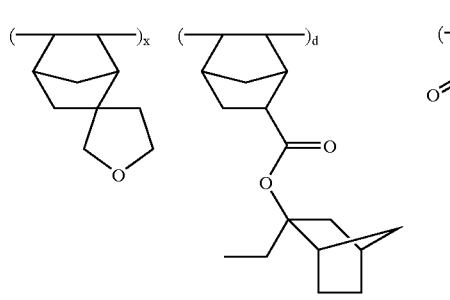

(x = 0.10, d = 0.40, e = 0.50, Mw = 8,700)

Polymer 3

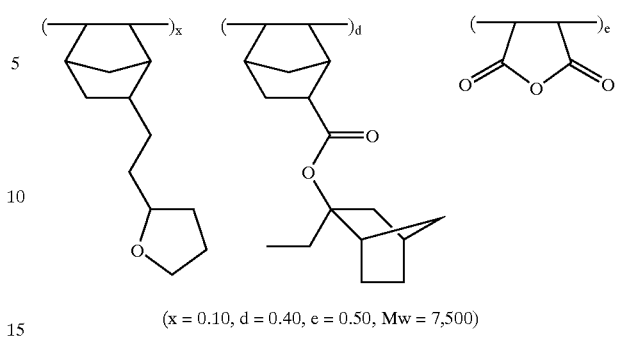

(x = 0.10, d = 0.40, e = 0.50, Mw = 7,500)

Reference Example 2

Resist compositions were formulated using the polymers obtained in Reference Examples as a base resin and examined for substrate adhesion.

Reference Examples 2-1 to 2-3 & Comparative Examples 1, 2

Resist compositions were prepared by blending the inventive polymers (Polymers 1 to 3) and comparative polymers (Polymers 4 and 5 shown below) as a base resin, a photoacid generator, a basic compound and a solvent in accordance with the formulation shown in Table 1. They were passed through a Teflon filter having a pore diameter of 0.2 µm, obtaining resist solutions.

Polymer 4

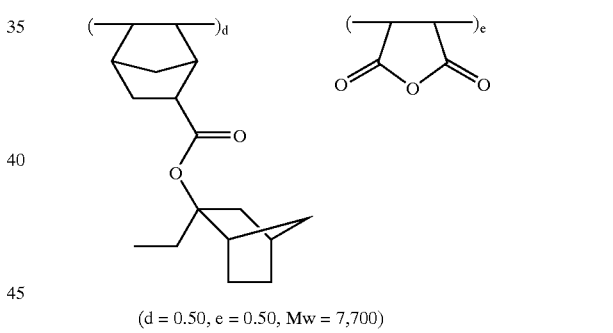

(d = 0.50, e = 0.50, Mw = 7,700)

Polymer 5

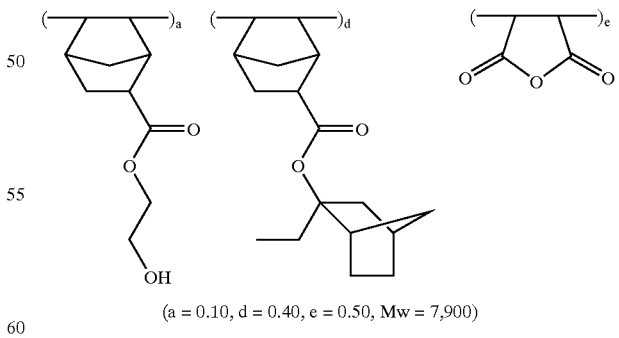

(a = 0.10, d = 0.40, e = 0.50, Mw = 7,900)

Each resist solution was spin coated on a silicon wafer having hexamethyldisilazane sprayed thereon at 90° C. for 40 seconds and heat treated at 110° C. for 90 seconds, forming a resist film of 0.5 µm thick. The resist film was exposed to light by means of a KrF excimer laser stepper (Nikon Corp., NA=0.5), heat treated at 110° C. for 90 seconds, and puddle developed in a 2.38% tetramethylammonium hydroxide aqueous solution for 60 seconds, thereby forming a 1:1 line-and-space pattern. The wafer as developed was observed under overhead SEM. The minimum line width left unstripped is regarded as the adhesion limit of a resist under test.

The formulation and test results of the resist compositions are shown in Table 1. Note that the photoacid generator and basic compound and solvent used are triphenylsulfonium trifluoromethanesulfonate (TPSTf), tributylamine (TBA), and propylene glycol methyl ether acetate (PGMEA), respectively. The solvent contained 0.01% by weight of surfactant FC-430 (Sumitomo 3M Co., Ltd.).

TABLE 1

| | Resin (pbw) | Photoacid generator (pbw) | Basic compound (pbw) | Solvent (pbw) | Adhesion limit ($\mu$m) |
|---|---|---|---|---|---|
| Reference Example | | | | | |
| 2-1 | Polymer 1 (80) | TPSTf (1) | TBA (0.078) | PGMEA (480) | 0.24 |
| 2-2 | Polymer 2 (80) | TPSTf (1) | TBA (0.078) | PGMEA (480) | 0.24 |
| 2-3 | Polymer 3 (80) | TPSTf (1) | TBA (0.078) | PGMEA (480) | 0.26 |
| Comparative Example | | | | | |
| 1 | Polymer 4 (80) | TPSTf (1) | TBA (0.078) | PGMEA (480) | >0.50 |
| 2 | Polymer 5 (80) | TPSTf (1) | TBA (0.078) | PGMEA (480) | >0.50 |

It is evident from Table 1 that polymers resulting from the inventive tetrahydrofuran compounds have significantly improved substrate adhesion.

Japanese Patent Application No. 2001-109755 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A tetrahydrofuran compound having the following general formula (1):

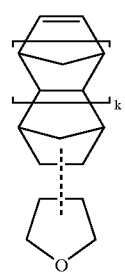

(1)

wherein the broken line represents a single bond, a divalent organic group, or a structure in which the alicyclic structure in the form of norbornene or tetracyclo[$4.4.0.1^{2,5}.1^{7,10}$] dodecene and the tetrahydrofuran cyclic structure share one or two constituent carbon atoms, and k is 0 or 1.

2. A tetrahydrofuran compound having the following general formula (2):

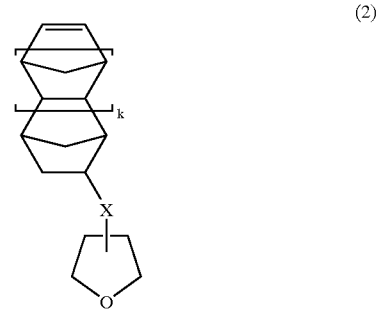

(2)

wherein X is a single bond or a group —$(CH_2)_m$— in which one or more methylene groups may be replaced by one or more oxygen atoms, m is an integer of 1 to 8, and k is 0 or 1.

3. A tetrahydrofuran compound having the following general formula (3):

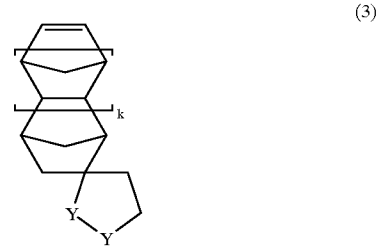

(3)

wherein one of two Y's is an oxygen atom and the other is a methylene group, and k is 0 or 1.

4. A tetrahydrofuran compound having the following general formula (4):

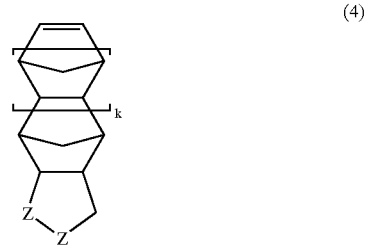

(4)

wherein one of two Z's is an oxygen atom and the other is a methylene group, and k is 0 or 1.

* * * * *